US012766045B2

(12) United States Patent
Quirk

(10) Patent No.: US 12,766,045 B2
(45) Date of Patent: Oct. 20, 2026

(54) AUTO-BIODEGRADABLE ABSORBENT ARTICLES

(71) Applicant: Kimberly-Clark Worldwide, Inc., Neenah, WI (US)

(72) Inventor: Stephen Quirk, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 776 days.

(21) Appl. No.: 18/006,040

(22) PCT Filed: Jul. 7, 2021

(86) PCT No.: PCT/US2021/040640

§ 371 (c)(1),
(2) Date: Jan. 19, 2023

(87) PCT Pub. No.: WO2022/026137

PCT Pub. Date: Feb. 3, 2022

(65) Prior Publication Data

US 2023/0346607 A1 Nov. 2, 2023

Related U.S. Application Data

(60) Provisional application No. 63/059,281, filed on Jul. 31, 2020.

(51) Int. Cl.

| | |
|---|---|
| ***A61F 13/15*** | (2006.01) |
| ***A61L 15/26*** | (2006.01) |
| ***A61L 15/36*** | (2006.01) |
| ***A61L 15/38*** | (2006.01) |

(52) U.S. Cl.

CPC ........ *A61F 13/15252* (2013.01); *A61L 15/26* (2013.01); *A61L 15/36* (2013.01); *A61L 15/38* (2013.01)

(58) Field of Classification Search

CPC .... A61L 15/38; A61L 15/36; A61F 13/15252; A61F 13/84

See application file for complete search history.

(56) References Cited

U.S. PATENT DOCUMENTS

| | | | | |
|---|---|---|---|---|
| 4,944,734 | A | 7/1990 | Wallach | |
| 6,160,199 | A * | 12/2000 | Noda | A61L 15/26 528/359 |
| 8,378,022 | B2 | 2/2013 | Bucevschi et al. | |
| 8,703,449 | B2 | 4/2014 | Martin et al. | |
| 8,821,854 | B2 | 9/2014 | Farmer et al. | |
| 2003/0012810 | A1 | 1/2003 | Cintio et al. | |
| 2005/0256471 | A1 | 11/2005 | Dibb et al. | |
| 2005/0261465 | A1 | 11/2005 | Nagarajan | |
| 2005/0282456 | A1 | 12/2005 | Zhao et al. | |
| 2008/0085297 | A1 | 4/2008 | Dave et al. | |
| 2010/0104615 | A1 | 4/2010 | Jiffer et al. | |
| 2019/0111176 | A1 | 4/2019 | Serna | |

FOREIGN PATENT DOCUMENTS

| | | | | |
|---|---|---|---|---|
| CN | 1051188 | A | 5/1991 | |
| CN | 1138299 | A | 12/1996 | |
| CN | 1139936 | A | 1/1997 | |
| CN | 1500114 | A | 5/2004 | |
| CN | 1501992 | A | 6/2004 | |
| CN | 1950112 | A | 4/2007 | |
| CN | 101195046 | A | 6/2008 | |
| CN | 102159598 | A | 8/2011 | |
| CN | 102665635 | A | 9/2012 | |
| CN | 103451201 | B | 12/2013 | |
| CN | 111278916 | A | 6/2020 | |
| EP | 1118342 | A1 | 7/2001 | |
| GB | 2484511 | A * | 4/2012 | A61L 15/36 |
| GB | 2492171 | A | 12/2012 | |
| JP | H07155180 | A | 6/1995 | |
| KR | 20180039995 | A | 4/2018 | |
| KR | 20180040118 | A | 4/2018 | |
| WO | WO1999029885 | A1 | 6/1999 | |
| WO | WO1999032536 | A1 | 7/1999 | |
| WO | WO2013137817 | A1 | 9/2013 | |

OTHER PUBLICATIONS

Mir et al. Urine Sodium. https://emedicine.medscape.com/article/2088449-overview#:~: text=Urine%20sodium%20(Na)%20analysis%20is, FENa):%201%2D2%25 (Year: 2018).*

Di et al., Biodegradation of polyhydroxybutyrate by *Pseudomonas* sp. DSDY0501 and purification and characterization of polyhydroxybutyrate depolymerase. 3 Biotech. Oct. 2019;9(10):359. doi: 10.1007/s13205-019-1871-9. Epub Sep. 7, 2019. PMID: 31544013; PMCID: PMC6732139. (Year: 2019).*

Wang et al., Structural insight into the poly(3-hydroxybutyrate) hydrolysis by intracellular PHB depolymerase from *Bacillus thuringiensis*, International Journal of Biological Macromolecules, vol. 284, Part 1, Jan. 2025. https://doi.org/10.1016/j.ijbiomac.2024.137999 (Year: 2025).* https://www.merriam-webster.com/dictionary/dispose%20of (Year: 2026).*

Chinese Office Action Corresponding to Application No. 202180051437.6 on Sep. 6, 2024.

Chinese Search Report Corresponding to Application No. 202180051437.6 on Mar. 20, 2024.

(Continued)

*Primary Examiner* — Ruth A Davis

(74) *Attorney, Agent, or Firm* — Dority & Manning, P.A.

(57) ABSTRACT

An auto-biodegradable absorbent article formed at least in part from a biodegradable polymer is provided that includes an inactivated microorganism product. The absorbent article contains one or more microorganisms that are designed to secrete an enzyme that degrades the biopolymer, which can be a polyhydroxybutyrate polymer. The microorganism can naturally secrete the enzyme or can be genetically modified to secrete the enzyme. The microorganisms or bacteria incorporated into the absorbent article are particularly selected based upon their salt tolerance and enzyme production at certain salt concentrations.

23 Claims, 3 Drawing Sheets

(56) References Cited

OTHER PUBLICATIONS

Keswick, Evaluation of the growth of microorganisms on diaper absorbent materials, Journal of Industrial Microbiology, vol. 3, Issue 1, 1988, pp. 21-28, https://doi.org/10.1007/BF01569438.
Savage et al., *Haladaptatus paucihalophilus* gen. nov., sp. nov., a halophilic archaeon isolated from a low-salt, sulfide-rich spring, International Journal of Systematic and Evolutionary Microbiology, vol. 57, 2007, pp. 19-24, https://doi.org/10.1099/ijs.0.64464-0
Swanson et al., Biodegradation of Organic Complexing Agents by WIPP-Indigenous Halophilic Microorganisms in Brines, Los Alamos National Laboratory, 2013, pp. 1-30.
Boyandin, A. N. et al., Microbial degradation of polyhydroxyalkanoates in tropical soils, International Biodeterioration & Biodegradation, 2013, vol. 83, pp. 77-84.
International Search Report and Written Opinion for PCT/US2021/040640 dated Oct. 22, 2021, 11 pages.
Vigneswari, S. et al., Extracellular polyhydroxyalkanoate depolymerase by acidovorax sp. DP5, Enzyme Research, 2015, vol. 2015, Article ID 212159, internal pp. 1-8.

* cited by examiner

AUTO-BIODEGRADABLE ABSORBENT ARTICLES

RELATED APPLICATIONS

The present application is the national stage entry of International Patent Application No. PCT/US2021/040640 having a filing date of Jul. 7, 2021, which claims priority to U.S. Provisional Application Ser. No. 63/059,281 having a filing date of Jul. 31, 2020, both of which are incorporated herein in their entirety by reference thereto.

BACKGROUND

Global production of petroleum-based plastics continues to increase every year. In recent years, for instance, over 300,000,000 metric tons of petroleum-based polymers have been produced. A significant portion of the above produced polymers are used to produce single-use products, such as plastic drinking bottles, straws, packaging, and absorbent articles, including wearable absorbent articles. Most of these plastic products are discarded and do not enter the recycle stream.

Particularly, absorbent articles, including personal care and child care garments, are currently made from predominantly petroleum-based plastics, such as films and nonwoven materials formed of polyethylene or polypropylene. Due to the nature of these articles, and the function they perform, it is difficult, if not impossible, to partially or completely recycle the polypropylene or polyethene materials used.

It has long been hoped that biodegradable polymers produced from renewable resources (hereinafter termed "biopolymers") would hold great promise in reducing the global accumulation of petroleum-based plastics in the environment. For example, significant research has been done on biologically derived polymers and on polymers that biodegrade in suitable environments. One such class of biopolymers are the polyhydroxyalkanoates. Specifically, polyhydroxybutyrate (PHB) shows promise in that the polymer is derived from natural sources, can be bio-degraded by several mechanisms, and is biocompatible with human tissues. Of particular advantage, polyhydroxybutyrate has thermoplastic properties that are very similar to some petroleum-based polymers.

Polyhydroxyalkanoates are synthesized using a variety of bacterial and archaea genera, including Halobacillus, *Bacillus, Salinobacter, Flavobacterium, Chromohalobacter, Halomonas, Marinobacter, Vibrio, Pseudomonas, Halococcus, Halorhabdus, Haladaptatus, Natrialba, Haloterrigena*, and *Halorussus*. The polyhydroxyalkanoate serves as an energy sink for these organisms. Production of polyhydroxyalkanoate polymers by the above microorganisms involves a three-step enzymatic mechanism that begins with acetyl coenzyme A. The final step of the pathway involves the polymerization of hydroxyalkanoic acid monomers into a polyhydroxyalkanoate polymer via a polyhydroxyalkanoate polymerase. Bio-synthesized polyhydroxyalkanoates accumulate in the bacterial cell as large molecular weight granules and can account for from about 60% to about 90% of the cellular dry mass.

Therefore, as polyhydroxyalkanoates can be broken down by a greater number of mechanisms that petroleum-based polymers, replacing petroleum-based polymers with biopolymers, such as polyhydroxyalkanoate polymers, would make significant advances in waste disposal processes. However, even though biopolymers are capable of biodegrading significantly faster than petroleum-based polymers, biopolymers can still remain in landfills or in the soil once discarded for significant periods of time. Thus, a need exists for a system and process for accelerating the decomposition of biopolymers, such as polyhydroxyalkanoates, once they enter the solid waste stream.

SUMMARY

In general, the present disclosure is directed to a biodegradable absorbent article. The biodegradable absorbent article is formed from at least one layer that includes a polyhydroxyalkanoate polymer and an inactivated microorganism product that includes at least one type of microorganism. The inactivated microorganism product is configured to activate upon contacting a salt containing liquid having a salt concentration of about 50 millimolar or greater, where the at least one type of microorganism produces an enzyme that degrades the polyhydroxyalkanoate polymer and increases a rate at which the polyhydroxyalkanoate polymer breaks down upon contact with the salt containing liquid.

In one aspect, the enzyme secreted by the at least one type of microorganism comprises poly[R-3-hydroxybutyrate] depolymerase. Particularly, in an aspect, the at least one type of microorganism is a naturally occurring bacterium that naturally encodes the enzyme. Additionally or alternatively, the at least one type of microorganism includes a genetically modified microorganism that has been genetically modified to secrete the enzyme. Nonetheless, in a further aspect, the at least one type of microorganism includes at least one type of bacterium that is salt tolerant from about 100 millimolar to about 3 molar. In yet a further aspect, the at least one type of microorganism is selected to be salt tolerant to a concentration of salt contained in urine, menses, feces, or a combination thereof. In another aspect, the at least one type of microorganism contained within the encapsulated microorganism product includes a bacterium or archaea selected from a bacterial genera comprising Halobacillus, *Bacillus, Salinobacter, Flavobacterium, Chromohalobacter, Halomonas, Marinobacter, Vibrio, Pseudomonas, Halococcus, Halorhabdus, Haladaptatus, Natrialba, Haloterrigena*, and *Halorussus*, or mixtures thereof. In one aspect, the at least one type of microorganism contained in the encapsulated microorganism product includes *Pseudomonas aeruginosa, Haladaptatus paucihalophilus, Halomonas aquamarina*, or a combination thereof. In one aspect, the at least one type of microorganism contained in the inactivated microorganism product is selected based on environmental variables in which the biodegradable article will be used or disposed, the environmental variables comprising temperature, salinity, and concentration of oxygen. Furthermore, in an aspect, at least 90% of the microorganisms contained in the inactivated microorganism product are viable.

Nonetheless, in one aspect, the inactivated microorganism product is freeze dried or contained in a dehydrated polymer carrier. In an aspect, the dehydrated polymer carrier includes a crosslinked polyacrylate. In another aspect, the dehydrated polymer carrier includes a starch-based polymer, a cellulose-based polymer, agarose, or a crosslinked polyvinyl alcohol polymer. In one aspect, the inactivated microorganism product is in the form of flakes, and/or particles, fibers, or a granular material.

In yet a further aspect, the at least one layer is a film layer or a nonwoven layer. Additionally or alternatively, the absorbent is formed from at least two layers, a first layer including a liquid permeable liner, a second layer including an outer cover, and an absorbent structure positioned in between the liquid permeable liner and the outer cover, the liquid permeable liner and the outer cover being made from a polyhydroxyalkanoate polymer. In one aspect, the at least one microorganism is present in the biodegradable article at a ratio of an amount of the at least one microorganism to an amount of polyhydroxyalkanoate polymer at a ratio of from about $1\times10^{1}$ cfu:1 g to about $1\times10^{10}$ cfu:1 g. Furthermore, in an aspect, the encapsulated microorganism product is added to the biodegradable article in an amount of from about 0.01% to about 10% by weight of the biodegradable article.

The present disclosure is further directed to a kit of parts that includes a biodegradable absorbent article according to the present disclosure, a container, and a salt-containing liquid.

The present disclosure is also generally directed to a method of disposing a biodegradable article. The method includes contacting a biodegradable article according to the present disclosure with a salt containing liquid. In one aspect, the biodegradable absorbent article is contacted with a bodily fluid, with a liquid having a salt content of from about of from about 100 millimolar to about 4 molar, or with both a bodily fluid and a liquid having a salt content of from about of from about 100 millimolar to about 4 molar. In a further aspect, the biodegradable article is a wearable absorbent article, and contacted with the bodily fluid during use by a user. In yet another aspect, the biodegradable article is placed into a container that contains the liquid having a salt content of about 3 molar or greater.

Other features and aspects of the present disclosure are discussed in greater detail below.

BRIEF DESCRIPTION OF THE DRAWINGS

A full and enabling disclosure of the present disclosure is set forth more particularly in the remainder of the specification, including reference to the accompanying figures, in which.

Figure 1:
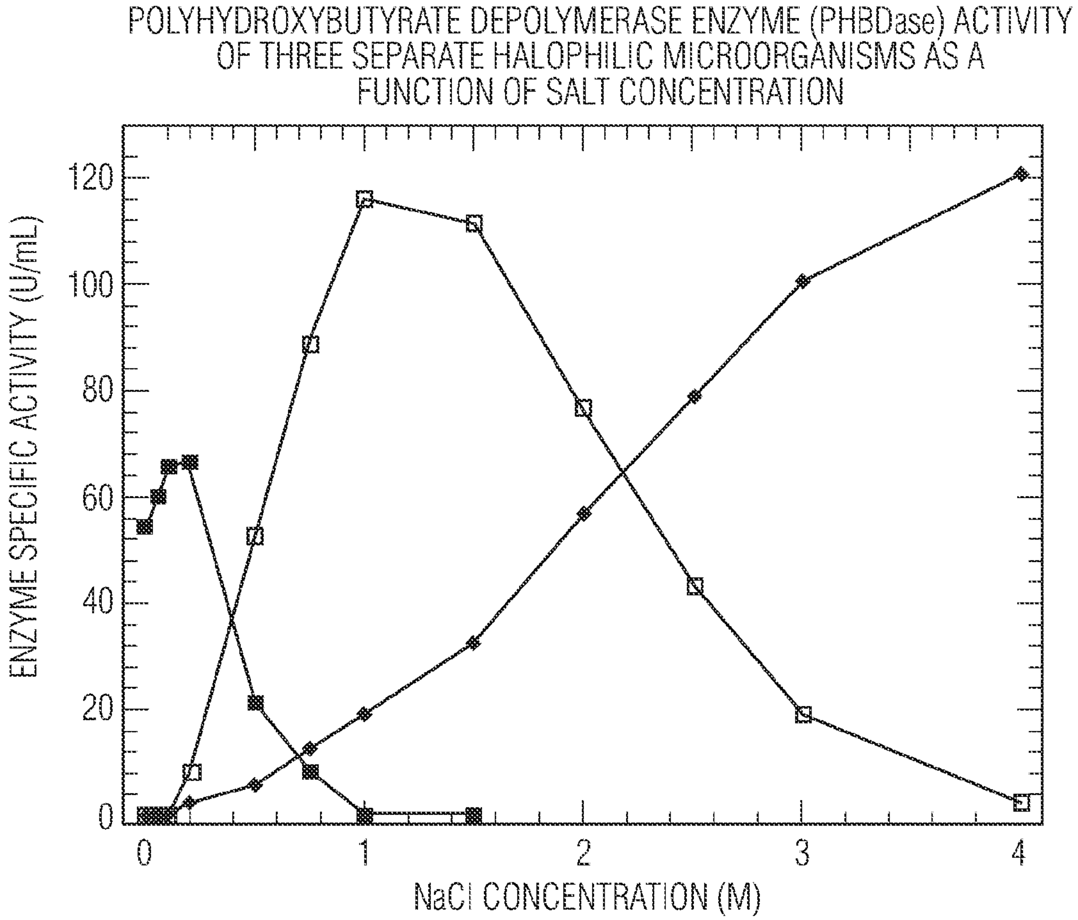
FIG. 1 is a graphical representation of polyhydroxybutyrate depolymerase enzyme (PHBDase) activity of three separate halophilic microorganisms as a function of salt concentration

Repeat use of reference characters in the present specification and drawings is intended to represent the same or analogous features or elements of the present invention.

DETAILED DESCRIPTION

Definitions

The terms "about," "approximately," or "generally,", when used herein to modify a value, indicates that the value can be raised or lowered by 10%, such as 7.5%, such as 5%, such as 4%, such as 3%, such as 2%, or such as 1%, and remain within the disclosed aspect.

The term "absorbent article" when used herein refers to products made from fibrous webs, alone or in combination with one or more films, which includes, but is not limited to, personal care absorbent articles, such as baby wipes, mitt wipes, diapers, pant diapers, open diapers, training pants, absorbent underpants, incontinence articles, feminine hygiene products (e.g., sanitary napkins), swim wear and so forth; medical absorbent articles, such as garments, fenestration materials, underpads, bedpads, bandages, absorbent drapes, and medical wipes; food service wipers; clothing articles; pouches, and so forth. Materials and processes suitable for forming such articles are well known to those skilled in the art. An absorbent article, for example, can include a liner, an outer cover, and an absorbent material or pad formed from a fibrous web positioned therebetween.

As used herein, the term "biodegradable" or "biodegradable polymer" generally refers to a material that degrades from the action of naturally occurring microorganisms, such as bacteria, fungi, and algae; environmental heat; moisture; or other environmental factors. The biodegradability of a material may be determined using ASTM Test Method 5338.92.

As used herein, the term "fibers" refer to elongated extrudates formed by passing a polymer through a forming orifice such as a die. Unless noted otherwise, the term "fibers" includes discontinuous fibers having a definite length and substantially continuous filaments. Substantially filaments may, for instance, have a length much greater than their diameter, such as a length to diameter ratio ("aspect ratio") greater than about 15,000 to 1, and in some cases, greater than about 50,000 to 1.

Detailed Description

It is to be understood by one of ordinary skill in the art that the present discussion is a description of exemplary embodiments only, and is not intended as limiting the broader aspects of the present disclosure.

Generally speaking, the present disclosure is directed to an absorbent article that is formed at least in part from biodegradable biopolymers, that contains one or more inactivated but viable microorganism, particularly selected to secrete an enzyme for significantly increasing the rate at which the biopolymers degrade. Particularly, the presents disclosure has found that an absorbent article formed at least in part by polyhydroxyalkanoate polymers, can be rapidly degraded using halophilic microorganisms, such as bacteria or archaea, that secrete an appropriate depolymerase enzyme in the presence of a salt containing liquid. Furthermore, the present disclosure has found that the degradation of the absorbent article can be further controlled based upon the salt tolerance of the microorganism selected, or by modifying a microorganism having the desired salt tolerance to express an appropriate depolymerase enzyme. For instance, it was surprisingly found that when a microorganism is selected based upon a specific salt tolerance, expression of an appropriate depolymerase enzyme, and thus, degradation of polyhydroxyalkanoate polymers can be further increased and/or slowed based upon the desired degradation rate.

For instance, as discussed above, in one aspect, the microorganism or collection of microorganisms that are contained in the inactivated microorganism product of the present disclosure can be selected not only in order to secrete a particular enzyme, but can also be selected based upon the environmental conditions in which the absorbent article will be disposed. For example, in one aspect, an absorbent article can be a wearable article meant to collect or contact one or more bodily fluids of a user. In such an aspect, it may be desirable for degradation of the absorbent article to begin immediately upon being saturated by the bodily fluid, which, in one aspect, may be urine, menses, or a bowel movement, for example. Particularly, as discussed above, microorganisms have a salt tolerance, which may be used herein to refer to a salt concentration, or range of concentrations at which the microorganism secretes an appropriate depolymerase enzyme, or a particular concentration of the appropriate depolymerase enzyme. Thus, in order to begin degradation upon contact with a bodily fluid, it would be desirable to select a microorganism that is tolerant at a concentration of a salt of about 50 millimolar (mM) to about 6 Molar (M), such as about 75 mM to about 4 M, such as about 100 mM to about 2.5 M, such as about 150 mM to about 2M, such about 200 mM to about 1.5 M, such as about 250 mM to about 1 M, or any ranges or values therebetween. For instance, a wearable article may contain one or more microorganisms tuned for contact with urine, and therefore may have a salt tolerance of about 200 mM to about 400 mM, or may be tuned for contact with menses, and have a salt tolerance of about 100 mM to about 200 mM, or alternatively, tuned for contact with a bowl movement and have a salt tolerance of about 50 mM to about 200 mM. Of course, as discussed, the wearable article may also include a single microorganism capable of producing an appropriate enzyme across all three ranges, or may instead include two or more, or three or more, microorganism, each microorganism being tuned for enzyme production at one or more of the above ranges.

This degree of salt tolerance may be further desirable for at-home, or non-commercial use, as, while still significantly decreasing the degradation time of the article, degradation may still require about 7 days or greater, such as about 14 days or greater, such as about 21 days or greater, such as about 30 days or greater, in a container or soil, allowing the user ample time to dispose of the article, or bag which contains the saturated article, prior to complete degradation. For instance, based upon the method and location of disposal (e.g. soil or ocean, to name a few), as well as temperature and other conditions, a standard biodegradable article generally takes 90 to 180 days to begin decomposition. Therefore, based upon the microorganism selected, and the amount thereof, a biodegradable article according to the present disclosure may degrade from about 10 times to about 100 times, or any range therebetween, faster than the same article that does not include the microorganism according to the present disclosure.

However, in one aspect, it can be desirable that the article be decomposed as quickly as possible, or it may be desirable to decompose of the article in an environment that kills or inactivates other bacteria present in the saturated article, such as a wearable article that has been soiled. In such an aspect, the microorganism may be selected to be tolerant of a concentration of a salt of about 3 M or greater, such as about 3.5 M or greater, such as about 4 M or greater, such as about 4.5 M or greater, such as about 5 M or greater, such as about 5.5 M or greater, such as about 6 M or greater, such as about 6.5 M or greater, such as about 7 M or greater, or any ranges or values therebetween. For instance, in such an aspect, the disposable article may be disposed of into a high salinity liquid, such as a container containing salt-water having a molar concentration of salt according to the above ranges, a commercial treatment facility, or a natural environment having a high degree of salinity. The high degree of salinity in conjunction with a microorganism having a tolerance for salt in that concentration may result in rapid degradation of the article, and may also kill other bacteria, such as dangerous bacteria, in the article that are not tolerant of the high salinity.

Nonetheless, it should be understood that, in one aspect, an absorbent article according to the present disclosure may include more than one microorganism, and may therefore be configured to degrade in any concentration of salt discussed above. In one such aspect, the article may begin to degrade upon contact with a low-saline solution, such as a bodily fluid in one aspect, which may begin the degradation process. The absorbent article may then be placed into a high-salinity environment which activates the high-salt tolerant microorganism and completing the degradation process started by the less-salt tolerant microorganism.

Furthermore, it should be understood that in one aspect, a microorganism may be selected for its salt-tolerance, and if the microorganism does not produce, or produce enough of an appropriate depolymerase enzyme, the microorganism may be modified with a gene to produce, or produce more of the targeted depolymerase enzyme. Thus, in one aspect, the microorganism selected can be a microorganism that naturally produces the desired enzyme or can be a microorganism that has been genetically modified or cloned in order to express the desired depolymerase gene.

Nonetheless, it should be understood that the microorganism is inactivated, and held in suspended animation until saturated by a salt containing liquid. For instance, in one aspect, the microorganism may be encapsulated, or may be freeze dried, such that the microorganism remains inactive until saturated with a salt-containing liquid. Thus, as will be discussed below, the inactivation method or material may be selected so as to allow diffusion of the microorganism or enzymes produced into the article upon saturation, but that does not allow premature diffusion prior to soiling or wetting the article with a salt containing liquid.

In general, any suitable microorganism can be selected for use in the product of the present disclosure that secretes a metabolite or enzyme capable of degrading a biopolymer, particularly a polyhydroxyalkanoate polymer. For instance, the one or more microorganisms can be one or more bacteria or archaea that either expresses a native or an exogenous poly(hydroxybutyrate) depolymerase enzyme. In one particular embodiment, the enzyme can be a poly[R-3-hydroxybutyrate] depolymerase enzyme. The following reaction, for instance, illustrates the enzymatic degradation of a polyhydroxybutyrate polymer by a poly[R-3-hydroxybutyrate] depolymerase.

(I)

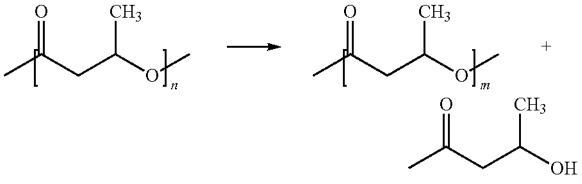

wherein m<<n and represents small oligomers.

As stated above, in one aspect, the enzyme or metabolite that breaks down the polyhydroxyalkanoate polymer can be a naturally occurring bacteria or archaea that naturally expresses the desired enzyme. For instance, in one aspect, the microorganism incorporated into the product of the present disclosure is selected from a variety of bacterial genera, archaeal genera, or both bacterial and archaeal genera, including, but not limited to, Halobacillus, *Bacillus, Salinobacter, Flavobacterium, Chromohalobacter, Halomonas, Marinobacter, Vibrio, Pseudomonas, Halococcus,*

*Halorhabdus, Haladaptatus, Natrialba, Haloterrigena*, and *Halorussus*. Particular bacterium well suited for use in the product of the present disclosure, for instance, include *Haladaptatus paucihalophilusm, Halomonas aquamarina, Pseudomonas aeruginosa*, or mixtures thereof. For instance, referring to FIG. 1, *Pseudomonas aeruginosa*, represented by the black squares, has a relatively low salt tolerance, and produces a moderate amount of an enzyme for breaking down polyhydroxyalkanoate polymers from very low salt concentrations to concentrations of about 1M. *Halomonas aquamarina*, represented by the hollow squares, has a moderate salt tolerance, and produces a large amount of enzyme from salt concentrations of about 100 mM to about 4 M. Additionally, *Haladaptatus paucihalophilusm* is very salt tolerate, and produces large amounts of enzyme from salt concentrations of about 100 mM to more than 4M. Therefore, while these bacteria and archaea have been shown as exemplary low salt-tolerant, moderately salt-tolerant, and high salt-tolerant microorganisms, the present disclosure has found that the microorganism, and amount thereof, can be carefully selected to provide an appropriate enzymatic response.

In addition to microorganisms that naturally express the depolymerase gene, one or more genetically modified bacteria or archaea may also be selected that express an exogenous depolymerase enzyme capable of breaking down a polyhydroxyalkanoate polymer. For example, in accordance with the present disclosure, any genus of bacterium or archaea can be matched with any polyhydroxyalkanoate depolymerase enzyme that is expressed from a constitutive vector coupled with the correct signal sequence. In this aspect, any suitable gram positive bacterium, gram negative bacterium, or archaea can be used to produce and secrete enzyme, which can be a gram positive polyhydroxyalkanoate depolymerase enzyme, for example. In this manner, the inactivated microorganism product of the present disclosure can be customized based on environmental variables, including the salinity of the desired disposal environment. In addition, the sequence of the enzyme can be matched to the environment by selecting one of approximately 6,400 depolymerase sequences that are known (e.g. NCBI database) or with a fully or partially engineered variant. In one aspect, the selected bacteria and/or archaea can be transformed with a plasmid vector which harbors a constitutively expressed gene in coding a poly[R-3-hydroxybutyrate] depolymerase that contains an appropriate N-ter signal sequence. Alternatively, the bacteria and/or archaea of choice can have the depolymerase gene inserted into its chromosome by transduction, linear recombination, or any other suitable method instead of using an extra chromosomal vector thereby eliminating the need for an exogenous vector.

When modifying a microorganism, any suitable gram positive bacteria, gram negative bacteria, and/or archaea may be used. For example, in one embodiment, the modified bacteria can be obtained from the genus Halobacillus, *Bacillus, Salinobacter, Flavobacterium, Chromohalobacter, Halomonas, Marinobacter, Vibrio, Pseudomonas, Halococcus, Halorhabdus, Haladaptatus, Natrialba, Haloterrigena*, and *Halorussus*.

In one aspect, the inactivated microorganism product of the present disclosure can include a combination of different bacteria and/or archaea. For example, in one aspect, the product can contain bacteria and/or archaea that naturally secrete the depolymerase enzyme combined with bacteria and/or archaea that have been genetically modified in order to secrete the depolymerase enzyme. The genetically modified bacteria and/or archaea, for instance, can be used to fine tune the system based on environmental conditions and feed supply.

Once one or more microorganisms have been selected for the product of the present disclosure, the one or more microorganisms are then inactivated, such as by freeze drying or combination with a polymer carrier. In one aspect, the polymer carrier is a material that is highly water absorbent without being water soluble. In one particular embodiment, for instance, the polymer carrier is in the form of a gel when combined with water, can be dehydrated into the form of a solid, and then capable of being rehydratable when contacted with moisture. In this manner, the one or more microorganisms can be combined with the polymer carrier in the form of a gel. Once blended together, water can then be removed in order to form a solid. The solid can be formed into any suitable shape and incorporated into the absorbent article. In order to degrade polymers forming the absorbent article, the solid material is contacted with moisture that causes the carrier polymer to rehydrate. Once rehydrated, the microorganisms can be released from the polymer gel or can secrete enzymes that are released from the polymer gel.

Various different materials can be used as the polymer carrier. For example, in one aspect, the polymer carrier can comprise a polyacrylate polymer, and particularly a crosslinked polyacrylate polymer. However, in another aspect, other polymers, such as polymethacrylamide, polyester, polyether and polyurethane, can be used. Particularly, as discussed above, various encapsulants may be used that rehydrate upon saturation with a liquid such that the microorganism, or a secreted enzyme thereof, may permeate through the encapsulant.

For example, in one embodiment, the carrier polymer can be a salt of polyacrylic acid that is polymerized with a crosslinking agent, such as a silane. For example, in one embodiment, the crosslinking agent can be a trimethoxysilane, such as methacryloxy-propyl-trimethoxysilane. The salt of polyacrylic acid can be a sodium salt and can be at least 40% neutralized, such as at least 50% neutralized, such as at least 60% neutralized, and less than about 90% neutralized, such as less than about 80% neutralized. The polymer can have any suitable degree of crosslinking and molecular weight so as to have a gel-like state when combined with water. For example, the polymer can have a molecular weight of greater than about 50,000 daltons, such as greater than about 100,000 daltons, such as greater than about 150,000 daltons, such as greater than about 200,000 daltons, such as greater than about 225,000 daltons, and generally less than about 500,000 daltons, such as less than about 300,000 daltons, such as less than about 275,000 daltons.

In addition to polyacrylate polymers, various other rehydratable polymers may be used as the carrier polymer in the product of the present disclosure. For example, in an alternative embodiment, the carrier polymer can be a starch, and particularly a starch copolymer. In an alternative embodiment, the carrier polymer can be a cellulose polymer, such as a methyl cellulose polymer, an ethyl cellulose polymer, or a carboxymethyl cellulose polymer. Other carrier polymers that may be used include agarose, dextran, a gelatin, a polyvinyl alcohol, and mixtures thereof. Particular examples of carrier polymers include hydrolysis products of starch-acrylonitrile graft copolymers, starch-acrylic acid graft copolymers, starch-styrenesulfonic acid graft copolymers, starch-vinylsulfonic acid graft copolymers, starch-acrylamide graft copolymers, cellulose-acrylonitrile graft copolymers, cellulose-styrenesulfonic acid graft copolymers, crosslinked carboxymethylcellulose, hyaluronic acid, agarose, crosslinked polyvinyl alcohols, crosslinked sodium polyacrylates, sodium acrylate-vinyl alcohol copolymers, saponification products of polyacrylonitrile polymers, and combinations of two or more thereof.

As described above, the carrier polymer can be in a gel-like state when combined with the one or more microorganisms. For example, when the one or more microorganism are combined with the carrier polymer, the carrier polymer can contain water in an amount greater than about 30% by weight, such as in an amount greater than about 40% by weight, such as in an amount greater than about 50% by weight, such as in an amount greater than about 60% by weight, such as in an amount greater than about 70% by weight, such as in an amount greater than about 80% by weight, and even in amounts greater than 90% by weight depending upon the particular carrier polymer chosen. The amount of water is generally less than about 99% by weight, such as less than about 95% by weight, such as less than about 80% by weight. When using a crosslinked polyacrylate polymer, for instance, the carrier polymer can contain water in an amount from about 55% to about 85% by weight including all increments of 1% by weight therebetween.

After the carrier polymer and one or more microorganisms are combined together, the carrier polymer can be dehydrated by removing water. For instance, water can be removed from the resulting mixture in order to form a solid product. The resulting solid product can contain water in an amount less than about 20% by weight, such as in an amount less than about 10% by weight, such as in an amount less than about 8% by weight, such as in an amount less than about 6% by weight, such as in an amount less than about 4% by weight, such as in an amount less than about 2% by weight. Water is generally contained in the solid product in an amount greater than about 0.01% by weight, such as in an amount greater than about 0.5% by weight.

In addition to one or more microorganisms, the inactivated microorganism product of the present disclosure can also contain various other additives and components. In one particular application, for instance, a biopolymer can be added to the inactivated microorganism in conjunction with the one or more microorganisms. The biopolymer, for instance, can be a polyhydroxyalkanoate, such as a polyhydroxybutyrate polymer. The polyhydroxyalkanoate polymer, for instance, can serve as a food source for the microorganism within the inactivated product and can prime the microorganism for producing desired depolymerase enzyme. In particular, adding a polyhydroxyalkanoate polymer into the inactivated product helps keep the metabolic functions of the microorganism focused on polyhydroxybutyrate degradation. The amount of polyhydroxyalkanoate polymer contained in the inactivated microorganism product can generally be about 0.1 mg to about 500 mg, such as about 1 mg to about 200 mg, such as about 10 mg to about 100 mg, or any ranges or values therebetween.

In addition to one or more microorganisms and a polyhydroxyalkanoate polymer, the inactivated microorganism product can also contain a sugar, such as glucose or trehalose and/or a protein source, such as bovine serum albumin.

Once the microorganisms and any additives and components are combined together and dehydrated and/or freeze dried, for example, to form a solid product, the solid product can be converted into any suitable size and shape for addition to an absorbent article. In one embodiment, for instance, the resulting mixture can be formed into a film or fibers. The fibers can then be chopped to any desired fiber size. For instance, the fibers can have an average fiber length of less than about 5 cm, such as less than about 3 cm, such as less than about 1 cm, and generally greater than about 0.01 mm, such as greater than about 0.1 mm, such as greater than about 0.5 mm.

When formed into a film, the film can be cut into the form of flakes. The flakes, for instance, can have an average particle size of less than about 10 mm, such as less than about 7 mm, such as less than about 5 mm, such as less than about 3 mm, and generally greater than about 0.1 mm, such as greater than about 0.5 mm.

In an alternative embodiment, the inactivated microorganism product can be in the form of particles or granules. The particles or granules, for instance can be the product of a grinding process. The particles or granules, for instance, can have an average particle size of less than about 10 mm, such as less than about 5 mm, such as less than about 4 mm, such as less than about 3 mm, and generally greater than about 0.01 mm, such as greater than about 0.1 mm, such as greater than about 0.5 mm, such as greater than about 1 mm.

Nonetheless, the resulting solid material represents an inactivated microorganism product. The amount of one or more microorganisms contained in the product can vary depending upon the particular microorganism selected, the carrier polymer selected (if any), any additives or components selected, and the biodegradable article for which the inactivated microorganism will be introduced in to. In general, the microorganism is present in the solid product in an amount of about $1\times10^1$ cfu to about $1\times10^{10}$ cfu per gram of solid product, such as about $1\times10^2$ cfu to about $1\times10^9$ per gram, such as about $1\times10^3$ cfu to about $1\times10^8$ cfu per gram, such as about $1\times10^4$ cfu to $1\times10^6$ cfu per gram of solid product, or any ranges or values therebetween.

Nonetheless, while it has been discussed above that the degree and rate of decomposition may be solely based upon the type of microorganism, the degree of salt tolerance, and the amount of enzyme producing capacity, in one aspect, the amount of inactivated microorganism incorporated into the absorbent article may also be carefully controlled to provide the desired degradation properties. Thus, in one aspect, the amount of the inactivated microorganism product added to the absorbent article, based upon the weight of the absorbent article in an amount of about 0.01 mg to about 10 grams of solid product per biodegradable article, such as about 1 mg to about 7.5 g, such as about 10 mg to about 5 g, such as about 50 mg to about 2.5, such as about 100 mg to about 1 g of solid product per biodegradable article, or any ranges or values therebetween. Thus, in one aspect, the solid product may be incorporated into the biodegradable article in an amount of about 0.001% to about 10% by weight of the absorbent article, such as about 0.01 to about 9%, such as about 0.1% to about 8%, such as about 0.5% to about 7%, such as about 1% to about 5%, or any ranges or values therebetween.

The inactivated microorganism product as described above can be included in an absorbent article for accelerating the degradation of biopolymers used to form the absorbent article, particularly polyhydroxyalkanoate polymers. The inactivated microorganism product in the form of particles, flakes, granules, or fibers, can be mixed into a layer of an absorbent article, or may be contained between two or more layers that form an absorbent article, where at least one of the layers is at least partially formed from a biodegradable polymer. Of course, it should be understood that, in one aspect, substantially all of at least one of the layers, or substantially all of both of the layers may be formed from a biodegradable polymer. Thus, after contacting the absorbent article with a salt containing liquid, the solid product that contains the inactivated microorganism product rehydrates and transforms into a gel-like state and releasing the microorganisms, or enzymes secreted therefrom, contained therein.

Nonetheless, in one aspect, the absorbent article includes at least one layer that is a nonwoven web formed completely or at least in part from a biodegradable polymer, or is a film formed completely or at least in part from a biodegradable polymer, or contains both a nonwoven layer and a film layer, where at least a portion of, or substantially all of, both the nonwoven layer and the film layer are formed from a biodegradable polymer. Of course, as discussed above, in one aspect, the nonwoven layer, the film layer, or both the nonwoven layer and the film layer are formed almost entirely from one or more biodegradable polymers.

Regardless, fibers formed from a biodegradable polymer may generally have any desired configuration, including monocomponent, multicomponent (e.g., sheath-core configuration, side-by-side configuration, segmented pie configuration, island-in-the-sea configuration, and so forth), and/or multiconstituent (e.g., polymer blend). In some embodiments, the fibers may contain one or more additional polymers as a component (e.g., bicomponent) or constituent (e.g., biconstituent) to further enhance strength and other mechanical properties. For instance, a thermoplastic composition may form a sheath component of a sheath/core bicomponent fiber, while an additional polymer may form the core component, or vice versa. The additional polymer may be a thermoplastic polymer that is not generally considered biodegradable, however such a polymer is generally used as a small component, if at all, of the fiber, such as about 25% or less, such as about 20% or less, such as about 15% or less, such as about 10% by less by weight of the fiber, and can include polymers, such as polyolefins, e.g., polyethylene, polypropylene, polybutylene, and so forth; polytetrafluoroethylene; polyesters, e.g., polyethylene terephthalate, and so forth; polyvinyl acetate; polyvinyl chloride acetate; polyvinyl butyral; acrylic resins, e.g., polyacrylate, polymethylacrylate, polymethylmethacrylate, and so forth; polyamides, e.g., nylon; polyvinyl chloride; polyvinylidene chloride; polystyrene; polyvinyl alcohol; and polyurethanes. More desirably, however, the additional polymer, particularly when polyhydroxyalkanoates (PHA) and/or polyhydroxybutyrates (PHB) are used, is biodegradable, such as aliphatic polyesters, such as polyesteramides, modified polyethylene terephthalate, polylactic acid (PLA) and its copolymers, terpolymers based on polylactic acid, polyglycolic acid, polyalkylene carbonates (such as polyethylene carbonate), polyhydroxyvalerates (PHV), polyhydroxybutyrate-hydroxyvalerate copolymers (PHBV), and polycaprolactone, and succinate-based aliphatic polymers (e.g., polybutylene succinate, polybutylene succinate adipate, and polyethylene succinate); or other aliphatic-aromatic copolyesters.

Any of a variety of processes may be used to form fibers in accordance with the present invention. For example, the composition described above may be extruded through a spinneret, quenched, and drawn into the vertical passage of a fiber draw unit. The fibers may then be cut to form staple fibers having an average fiber length in the range of from about 3 to about 80 millimeters, in some embodiments from about 4 to about 65 millimeters, and in some embodiments, from about 5 to about 50 millimeters. The staple fibers may then be incorporated into a nonwoven web as is known in the art, such as bonded carded webs, through-air bonded webs, etc. The fibers may also be deposited onto a foraminous surface to form a nonwoven web. Of course, other methods for forming nonwoven webs, including meltblown webs, may be used, so long as they are compatible with the biodegradable polymers.

Of course, as mentioned above, in one aspect, the biodegradable polymer may also be used to form a film. The film may be mono- or multi-layered. Multilayer films may be prepared by co-extrusion of the layers, extrusion coating, or by any conventional layering process. Such multilayer films normally contain at least one base layer and at least one skin layer, but may contain any number of layers desired. For example, the multilayer film may be formed from a base layer and one or more skin layers. In such aspects, the skin layer(s) may be formed from any film-forming polymer, such as any of the copolymers discussed above. If desired, the skin layer(s) may contain a softer, lower melting polymer or polymer blend that renders the layer(s) more suitable as heat seal bonding layers for thermally bonding the film to a nonwoven web. However, if one aspect, the film is formed substantially exclusively from biodegradable polymers.

Regardless of whether the biodegradable polymer is used to form a nonwoven layer, a film layer, or both a film layer and a nonwoven layer, additives as known in the art may be incorporated into the polymer compositions prior to formation of the layer.

In one aspect, the absorbent article includes, for example, diapers, training pants, swim pants, adult incontinence products, feminine hygiene products, and the like. These products typically include a water permeable liner, an outer cover, and an absorbent structure positioned in between the liquid permeable liner and the outer cover. In the past, the liquid permeable liner and the outer cover were primarily made from petroleum-based polymers. However, absorbent articles according to the present disclosure may replace the petroleum-based polymers with biopolymers, such as polyhydroxybutyrate. Consequently, absorbent articles may contain biopolymers in amounts greater than about 5% by weight, such as in amounts greater than about 10% by weight, such as in amounts greater than about 20% by weight, such as in amounts greater than about 30% by weight, such as in amounts greater than about 40% by weight, such as in amounts greater than about 50% by weight, such as in amounts greater than about 60% by weight, such as in amounts greater than about 70% by weight, based upon the weight of the absorbent article. Alternatively, in one aspect, the above weight percentages can refer to a weight percentage of the polymers in the article that are biodegradable.

Figure 2:
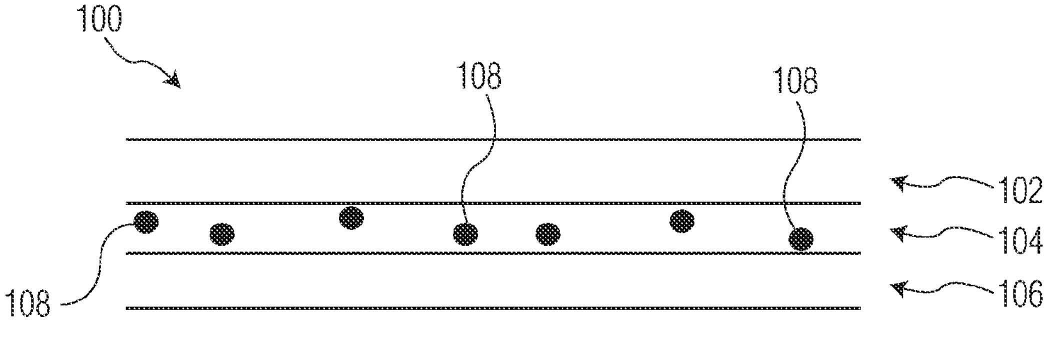
FIG. 2 is a cross-sectional view of an absorbent article according to an aspect of the present disclosure.

Referring to FIG. 2, in one aspect, an absorbent article according to the present disclosure can include multiple layers, one or more of which contain the inactivated microorganism(s). In one aspect, the absorbent article 100 includes an inner layer 102, such as a liquid permeable bodyside liner, an absorbent core 104, and an outer layer 106, such as an outer cover, which may be generally impermeable to liquids while remaining permeable to vapors. As shown in FIG. 2, in one aspect, the inactivated microorganism(s) 108 may be contained in the absorbent core layer 104 so as to become saturated with a liquid upon insult by a wearer of the absorbent article. However, it should be understood that, in one aspect, the inactivated microorganisms may be contained in any of the layers that are contacted with a salt containing liquid. Regardless, in one aspect, the inner layer 102 may be formed from one or more nonwoven webs, laminated to the outer layer 104 which may include one or more films, with an absorbent core 104 contained therebetween.

Figure 3:
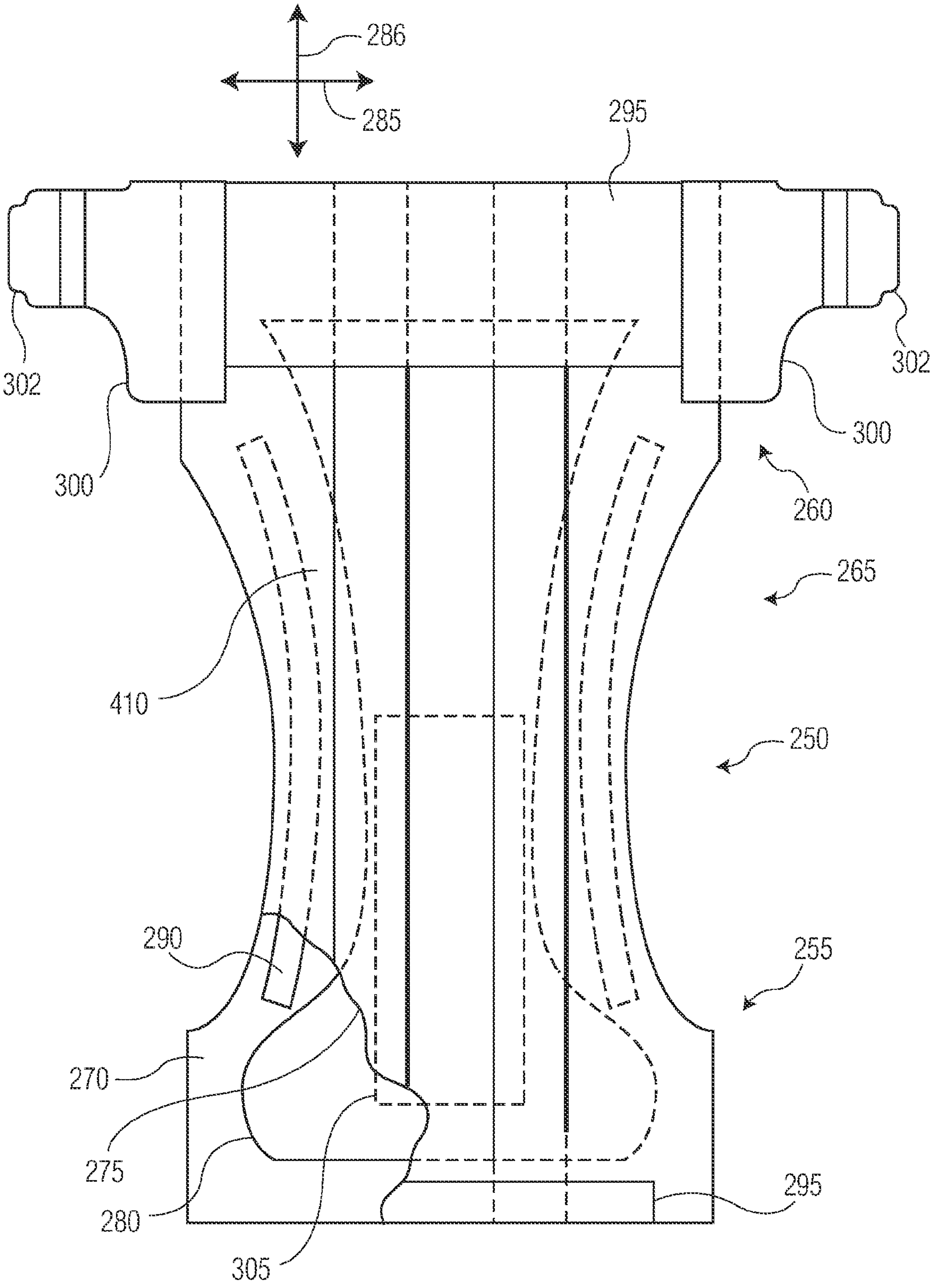
FIG. 3 is a top view of an absorbent article according to an aspect of the present disclosure.

Nonetheless, referring to FIG. 3, in one aspect the absorbent article includes a disposable diaper 250 that generally defines a front waist section 255, a rear waist section 260, and an intermediate section 265 that interconnects the front and rear waist sections. The front and rear waist sections 255 and 260 include the general portions of the diaper which are constructed to extend substantially over the wearer's front and rear abdominal regions, respectively, during use. The intermediate section 265 of the diaper includes the general portion of the diaper that is constructed to extend through the wearer's crotch region between the legs. Thus, the intermediate section 265 is an area where repeated liquid surges typically occur in the diaper.

The diaper 250 includes, without limitation, an outer cover, or backsheet 270, a liquid permeable bodyside liner, or topsheet, 275 positioned in facing relation with the backsheet 270, and an absorbent core body, or liquid retention structure, 280, such as an absorbent pad, which is located between the backsheet 270 and the topsheet 275. The backsheet 270 defines a length, or longitudinal direction 286, and a width, or lateral direction 285 which, in the illustrated embodiment, coincide with the length and width of the diaper 250. The liquid retention structure 280 generally has a length and width that are less than the length and width of the backsheet 270, respectively. Thus, marginal portions of the diaper 250, such as marginal sections of the backsheet 270 may extend past the terminal edges of the liquid retention structure 280. In the illustrated embodiments, for example, the backsheet 270 extends outwardly beyond the terminal marginal edges of the liquid retention structure 280 to form side margins and end margins of the diaper 250. The topsheet 275 is generally coextensive with the backsheet 270 but may optionally cover an area that is larger or smaller than the area of the backsheet 270, as desired.

To provide improved fit and to help reduce leakage of body exudates from the diaper 250, the diaper side margins and end margins may be elasticized with suitable elastic members, as further explained below. For example, as representatively illustrated in FIG. 3, the diaper 250 may include leg elastics 290 constructed to operably tension the side margins of the diaper 250 to provide elasticized leg bands which can closely fit around the legs of the wearer to reduce leakage and provide improved comfort and appearance. Waist elastics 295 may also be employed to elasticize the end margins of the diaper 250 to provide elasticized waistbands. The waist elastics 295 are configured to provide a resilient, comfortably close fit around the waist of the wearer. The composite of the present invention may be suitable for use as the leg elastics 290 and/or waist elastics 295.

As is known, fasteners 302 (e.g., hook and loop fasteners, buttons, pins, snaps, adhesive tape fasteners, cohesives, fabric-and-loop fasteners, etc.) may be employed to secure the diaper 250 on a wearer. In the illustrated embodiment, the diaper 250 includes a pair of side panels 300 (or ears) to which the fasteners 302, indicated as the hook portion of a hook and loop fastener, are attached. Generally, the side panels 300 are attached to the side edges of the diaper in one of the waist sections 255, 260 and extend laterally outward therefrom. The side panels 300 may be elasticized or otherwise rendered elastic by use of the composite of the present invention.

The diaper 250 may also include a surge management layer 305, located between the topsheet 275 and the liquid retention structure 280, to rapidly accept fluid exudates and distribute the fluid exudates to the liquid retention structure 280 within the diaper 250. The diaper 250 may further include a ventilation layer (not illustrated), also called a spacer, or spacer layer, located between the liquid retention structure 280 and the backsheet 270 to insulate the backsheet 270 from the liquid retention structure 280 to reduce the dampness of the garment at the exterior surface of a breathable outer cover, or backsheet, 270. Examples of suitable surge management layers 305 are described in U.S. Pat. No. 5,486,166 to Bishop and U.S. Pat. No. 5,490,846 to Ellis.

As representatively illustrated in FIG. 3, the disposable diaper 250 may also include a pair of containment flaps 410 which are configured to provide a barrier to the lateral flow of body exudates. The containment flaps 410 may be located along the laterally opposed side edges of the diaper adjacent the side edges of the liquid retention structure 280. Each containment flap 310 typically defines an unattached edge that is configured to maintain an upright, perpendicular configuration in at least the intermediate section 265 of the diaper 250 to form a seal against the wearers body. The containment flaps 410 may extend longitudinally along the entire length of the liquid retention structure 280 or may only extend partially along the length of the liquid retention structure. When the containment flaps 410 are shorter in length than the liquid retention structure 280, the containment flaps 410 can be selectively positioned anywhere along the side edges of the diaper 250 in the intermediate section 265. Such containment flaps 410 are generally well known to those skilled in the art. For example, suitable constructions and arrangements for containment flaps 410 are described in U.S. Pat. No. 4,704,116 to Enloe. Also, if desired, the containment flaps 410 may be elasticized or otherwise rendered elastic by use of the composite of the present invention.

The diaper 250 may be of various suitable shapes. For example, the diaper may have an overall rectangular shape, T-shape or an approximately hour-glass shape. In the shown embodiment, the diaper 250 has a generally I-shape. Other suitable components which may be incorporated on absorbent articles of the present invention may include waist flaps and the like which are generally known to those skilled in the art. Examples of diaper configurations suitable for use in connection with the biodegradable polymer of the present invention that may include other components suitable for use on diapers are described in U.S. Pat. No. 4,798,603 to Meyer et al.; U.S. Pat. No. 5,176,668 to Bernardin; U.S. Pat. No. 5,176,672 to Bruemmer et al.; U.S. Pat. No. 5,192,606 to Proxmire et al.; and U.S. Pat. No. 5,509,915 to Hanson et al.

The various regions and/or components of the diaper 250 may be assembled together using any known attachment mechanism, such as adhesive, ultrasonic, thermal bonds, etc. Suitable adhesives may include, for instance, hot melt adhesives, pressure-sensitive adhesives, and so forth. When utilized, the adhesive may be applied as a uniform layer, a patterned layer, a sprayed pattern, or any of separate lines, swirls or dots. In the illustrated embodiment, for example, the topsheet 275 and backsheet 270 may be assembled to each other and to the liquid retention structure 280 with lines of adhesive, such as a hot melt, pressure-sensitive adhesive. Similarly, other diaper components, such as the elastic members 290 and 295, fastening members 302, and surge layer 305 may be assembled into the article by employing the above-identified attachment mechanisms.

Although various configurations of a diaper have been described above, it should be understood that other diaper and absorbent article configurations are also included within the scope of the present invention. In addition, the present invention is by no means limited to diapers. In fact, several examples of absorbent articles are described in U.S. Pat. No. 5,649,916 to DiPalma, et al.; U.S. Pat. No. 6,110,158 to Kielpikowski; U.S. Pat. No. 6,663,611 to Blaney, et al. Further, other examples of personal care products that may incorporate such materials are training pants (such as in side panel materials) and feminine care products. By way of illustration only, training pants suitable for use with the present invention and various materials and methods for constructing the training pants are disclosed in U.S. Pat. No. 6,761,711 to Fletcher et al.; U.S. Pat. No. 4,940,464 to Van Gompel et al.; U.S. Pat. No. 5,766,389 to Brandon et al.; and U.S. Pat. No. 6,645,190 to Olson et al.

The present disclosure may be better understood with reference to the following example.

EXAMPLE

The following example demonstrates some of the benefits and advantages of the present disclosure.

Example 1

In this example, *Haladaptatus paucihalophilus* was evaluated for its viability during encapsulation according to the present disclosure and for its ability to degrade polyhydroxybutyrate films. *Haladaptatus paucihalophilus* was tested as it naturally produces PHBDase.

Organism and growth conditions: The bacterium *Haladaptatus paucihalophilus* was obtained from the American Type Culture Collection (ATCC BAA-1313). Cells were propagated in liquid culture or on agar plates in media A that contained (per 1 L): 5.0 g yeast extract, 5.0 g casamino acids, 1.0 g Na-glutamate, 2.0 g KCl, 3.0 g $Na_3$-citrate, 20.0 g $MgSO_4$-$7H_2O$, 200.0 g NaCl, 36.0 g $FeCl_2$-$4H_2O$, 0.5 g $MnCl_2$-$4H_2O$ (and 15 g agar for plating). In this example, mid-log phase *H. paucihalophilus* cultures were centrifuged for 4 mins at a speed of 10,000×g, washed in PBS, recentrifuged, and resuspended in a liquid media B composed of (per 1 L): 7.0 g $Na_2HPO_4$-$7H_2O$, 3.0 g $KH_2PO_4$, 1 g $NH_4Cl$, 5.0 g casamino acids, 1.0 g Na-glutamate, 2.0 g KCl, 3.0 g $Na_3$-citrate, 20.0 g $MgSO_4$-$7H_2O$, 200.0 g NaCl, 36.0 g $FeCl_2$-$4H_2O$, 0.5 g $MnCl_2$-$4H_2O$, 4.0 g granulated poly(3-hydroxybutyrate). All growth was at 50° C.

PHB film preparation: PHB was solvent cast using chloroform. PHB granules were dissolved in chloroform at 70° C., with constant stirring to a final concentration of 1.0 mg/mL. Typical time for complete dissolution was 60 minutes. The solution was then poured onto a 25° C. 5.0 cm×5.0 cm glass slide (2.0 mLs typical poured volume) and air dried for 24 hours. Typically, the films were further aged for five days (air atmosphere at 25° C.) and vacuum dried for three hours prior to use.

Encapsulated *H. paucihalophilus*: A mid-log culture of *H. paucihalophilus* in media B was lyophilized after the addition of trehalose (final concentration of 5% w/v) and bovine serum albumin (final concentration 1 mg/mL). Polyacrylic acid, sodium salt (70% neutralized), that is polymerized with methacryloxy-propyl-trimethoxysilane, was obtained from Evonik Corporation (Richmond VA, designated as polymer SR1717). It is 250 kDa oligomer and is supplied as a 32% (wt/wt) solids in a water solution. 1 g of the lyophilized mixture was added per 5 mLs of the polyacrylate with gentle mixing and the sample was poured into the wells of a 6-well culture plate. The samples were cured in a convection oven at 40° C. for 30 minutes to drive off the water. As the water is removed, the silanol groups on the polymer chain begin to crosslink, forming a lightly cross-linked polyacrylate hydrogel. Samples were stored at 10° C. until used.

Enzymatic reaction conditions. A turbidometric assay was employed to measure PHBDase activity under various conditions. The standard reaction (final volume=1.0 mL) contained 200 mg/L of PHB granules (that were previously stably suspended via sonication), 1 mM CaCl2), 25 mM buffer at various pH values. The reaction was initiated after the addition of enzyme and monitored at 650 nm in Applied Photophysics spectrapolarometer in absorbance mode. The reaction was gently stirred and maintained at a constant temperature. OD measurements (typically starting in the range of 2-3) were converted to percent OD remaining as a function of time.

Synthetic urine composition: A model urine was created with the following composition (per 1 L): 0.7 g KH2PO4, 0.3 g Ca(H2PO4)-2H2O, 0.5 g MgSO4-7H2O, 1.3 g Na3PO4-12H2O, 4.5 g NaCl, 3.2 g KCl, 8.6 g urea, 0.5 g creatinine, 0.2 g uric acid, 0.2 g glucose, 0.03 g human serum albumin.

PHB film biodegradation assays: A 1 cm diameter plug of the encapsulated material was centered on top of the PHB film on the glass slide. That set-up was placed into a petri dish and covered with moist potting soil. At 1-day intervals, the glass slide was removed from the petri dish, gently washed with distilled water and dried under vacuum at 50° C. for an hour in order to drive off all fluid. The residual encapsulated material was removed and the PHB film/glass slide was weighed. The mass of degraded PHB was calculated as:

$$((\text{film/slide mass at } t=0) - \text{slide mass}) - ((\text{film/slide mass at } t_n) - \text{slide mass})$$

The percent mass loss was then defined as:

$$[1 - (\text{film mass at } t_n / \text{film mass at } t=0)] \times 100$$

All assays were performed in triplicate and averaged.

Figure 4A:
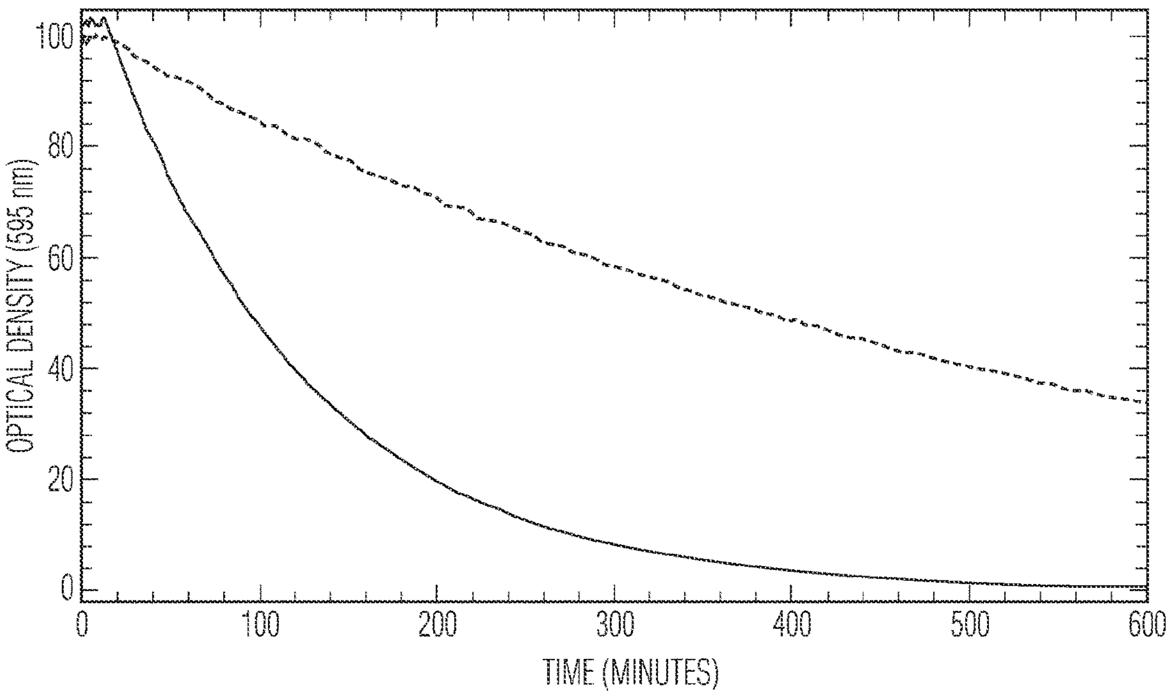
FIG. 4A is a graphical representation of polyhydroxybutyrate (PHB) degradation by *Haladaptatus paucihalophilus* PHBDase.
Figure 4B:
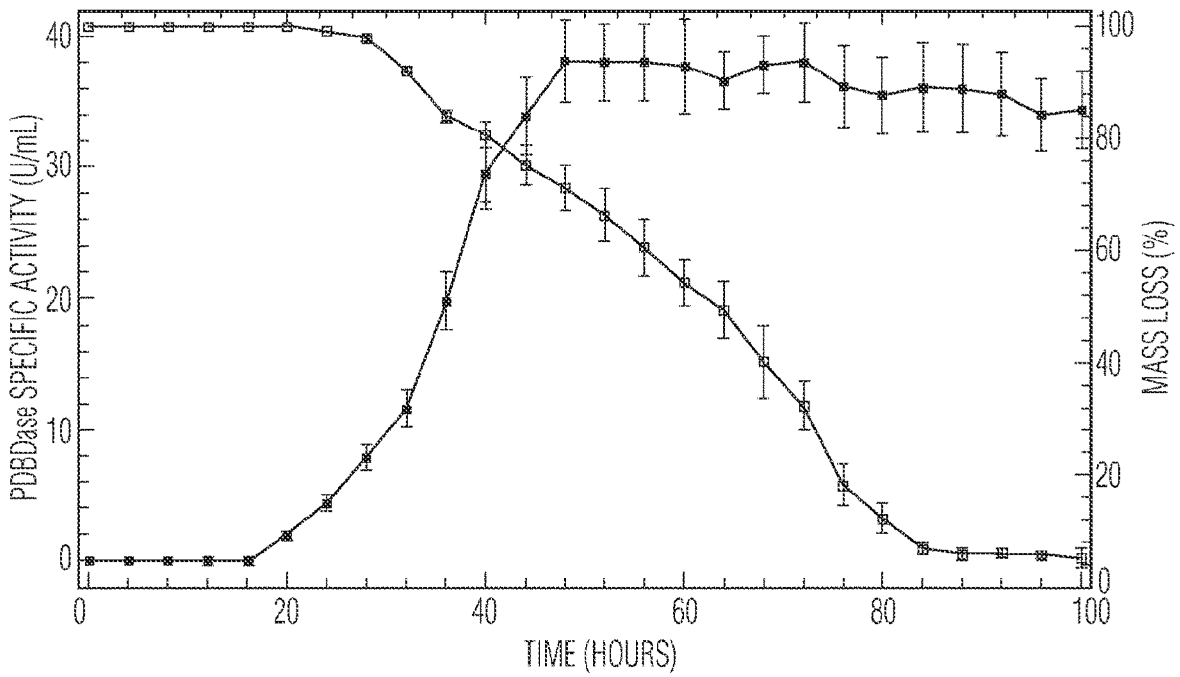
FIG. 4B is a graphical representation of specific activity of *Haladaptatus paucihalophilus* PHBDase and loss of PHB film mass loss.

Scheme (I) above shows the reaction that is being measured in the enzyme assays of the present example. Solid PHB (as granules or film) is degraded to small oligomers and monomers. FIG. 4A shows that in fact, *H. paucihalophilus* produces an active PHBDase that is capable of degrading PHB in an in vitro assay. FIG. 4B shows that *H. paucihalophilus* not only produces an active PHB degrading enzyme, but that the intact (native) enzyme is secreted into the lightly crosslinked hydrogel and then diffuses into the surrounding medium where it contacts PHB substrate (as granules or as a PHB film). Once in the medium, the enzyme can be assayed for activity. The enzyme is capable of degrading PHB in a time dependent manner. The PHB sample film is fully degraded (as measured by loss of mass) over a 100 hour time course experiment. Over this same time course, the encapsulated *H. paucihalophilus* continue to produce and secrete active enzyme into the lightly crosslinked hydrogel, which in turn continuously diffuses into the medium and into contact with the remaining film.

Example 2

In Example 2, *Escherichia coli* was genetically modified to produce the PHBDase enzyme. As shown, enzyme was successfully produced and purified from the modified bacteria.

Production of an expression vector. The amino acid sequence of the *H. paucihalophilus* PHBDase (WP_0007977722.1) was utilized to construct a recombinant DNA expression system. A sequence: MHHHHHHGSENLYFQG was added to the amino terminus of the protein sequence after the first 23 amino acid signal sequence was removed. This sequence provides a 6-histidine nickel chelating sequence followed by the TEV protease cleavage site. Upon cleavage the recombinant protein will have an N-ter sequence that begins GLSGAS. This new sequence was reverse translated to DNA and codon optimized for expression in *E. coli* using the program Gene Designer from ATUM, Inc. The gene was assembled using standard PCR techniques by ATUM, Inc. and cloned into the expression vector p454-MR ($amp^r$, medium strength ribosomal binding site). The insert was verified by DNA sequencing after construction.

Expression and purification of the enzyme. The expression plasmid was used to transform chemically competent *E. coli* (BL21(DE3)) bacteria. Single colonies were selected from LB-Amp plates and used for expression screening. Colonies were grown at 30° C. for 12 hours in LB media supplemented with 100 μg/mL ampicillin. This culture was used to inoculate fresh LB-AMP flasks at a 1:100 inoculum. These cultures were grown at 20° C. until OD595=0.4 (typically 4 hours) at which time IPTG was added to a final concentration of 1 mM. Growth was continued for 12 hours. Cells were harvested by centrifugation at 10,000×g for 15 minutes and frozen at −80° C. until use (minimal time frozen was 24 hours). Cells were thawed on ice and were resuspended in Buffer A (0.5 M NaCl, 20 mM Tris-HCl, 5 mM imidazole, pH 7.9) (typically 1 mL per gram of cells). Cells were disrupted via two passes through a French Press followed by centrifugation at 30,000×g for 30 minutes. The crude extract was mixed with an equal volume of charged His-Bind resin slurry and the mixture was poured into 5 cm×4.9 cc column. The column was washed with 10 column volumes of was buffer (0.5 M NaCl, 20 mM Tris-HCl, 60 mM imidazole, pH 7.9) at a flow rate of 0.2 mL/min. PHBDase was eluted from the column with the addition of 3 column volumes of 0.5 M NaCl, 20 mM Tris-HCl, 1.0 M imidazole, pH 7.9. Fractions were collected (1.0 mL). Fractions containing enzyme were pooled after analysis by SDS PAGE. The pooled fractions were applied to a 70 cm×4.9 cc Sephadex G-100 column (10 mM Tris-HCl, pH 7.5, 1 mM EDTA). Fractions containing homogeneous PHBDase were pooled (after inspection by SDS PAGE), concentrated to 5 mg/mL via Centricon filters. Enzyme was stored frozen at −20° C. until use. The histidine tag was removed from the enzyme using TEV protease. Protein was diluted to 1.0 mg/mL into 10 mM Tris-HCl, pH 7.5, 25 mM NaCl. 100 U of TEV protease was added per mg of enzyme (approximate ratio of 1:100 (w/w). The reaction was allowed to proceed for 16 h at 4° C. The mixture was passed over a charged nickel column. One column volume of eluent was collected representing purified tag-free enzyme.

Example 3

As briefly discussed above, two further microorganisms were analyzed in addition to *Haladaptatus paucihalophilus* to determine salt tolerance and the presence of secreted PHBDase at various salt concentrations. Three bacteria: *Pseudomonas aeruginosa, Halomonas aquamarina*, and *Haladaptatus paucihalophilus* were encapsulated as described in Example 1. A 1 $cm^2$ plug of the encapsulated material was placed on top of a PHB film (on a glass slide). That set-up was placed into a petri dish and was submerged with a buffer composed of 25 mM PIPES (pH 6.5) and various amounts of NaCl. The dishes were incubated at 30° C. for 48 hours. At that point a 50 μL aliquot was removed and assayed for enzymatic activity. The enzyme specific activity is plotted as a function of salt concentration as shown in FIG. 1.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. A biodegradable absorbent article, comprising:

at least a first layer comprising a polyhydroxyalkanoate polymer; and an inactivated microorganism product, the inactivated microorganism product comprising at least one type of microorganism, wherein the inactivated microorganism product is contained in a dehydrated polymer carrier; and wherein the inactivated microorganism product activates upon contacting a salt containing liquid having a salt concentration of about 50 millimolar or greater, wherein the at least one type of microorganism produces an enzyme that degrades the polyhydroxyalkanoate polymer and increases a rate at which the polyhydroxyalkanoate polymer breaks down upon contact with the salt containing liquid.

2. The biodegradable absorbent article as defined in claim 1, wherein the enzyme secreted by the at least one type of microorganism comprises poly[R-3-hydroxybutyrate] depolymerase.

3. The biodegradable absorbent article as defined in claim 1, wherein the inactivated microorganism product is freeze dried.

4. The biodegradable absorbent article as defined in claim 1, wherein the at least one type of microorganism is a naturally occurring bacterium that naturally encodes the enzyme.

5. The biodegradable absorbent article as defined in claim 1, wherein the at least one type of microorganism comprises a genetically modified microorganism that has been genetically modified to secrete the enzyme.

6. The biodegradable absorbent article as defined in claim 1, wherein the at least one type of microorganism comprises at least one type of bacterium that is salt tolerant from about 100 millimolar to about 3 molar.

7. The biodegradable absorbent article as defined in claim 1, wherein the at least one type of microorganism is salt tolerant to a concentration of salt contained in urine, menses, feces, or a combination thereof.

8. The biodegradable absorbent article as defined in claim 1, wherein the at least one layer is a film layer or a nonwoven layer.

9. The biodegradable absorbent article as defined in claim 1, wherein the absorbent article includes at least two layers, the first layer comprising a liquid permeable liner, a second layer comprising an outer cover, and an absorbent structure positioned in between the liquid permeable liner and the outer cover, the liquid permeable liner and the outer cover being made from a polyhydroxyalkanoate polymer.

10. The biodegradable absorbent article as defined in claim 1, wherein the at least one microorganism is present in the biodegradable article at a ratio of an amount of the at least one microorganism to an amount of polyhydroxyalkanoate polymer of from about $1\times10^{1}$ cfu:1 g to about $1\times10^{10}$ cfu:1 g.

11. The biodegradable absorbent article as defined in claim 1, wherein the inactivated microorganism product is added to the biodegradable article in an amount of from about 0.01% to about 10% by weight of the biodegradable article.

12. The biodegradable absorbent article as defined in claim 1, wherein the at least one type of microorganism comprises a bacterium or archaea selected from a bacterial genera comprising Halobacillus, *Bacillus, Salinobacter, Flavobacterium, Chromohalobacter, Halomonas, Marinobacter, Vibrio, Pseudomonas, Halococcus, Halorhabdus, Haladaptatus, Natrialba, Haloterrigena*, and *Halorussus*, or mixtures thereof.

13. The biodegradable absorbent article as defined in claim 1, wherein the at least one type of microorganism comprises *Pseudomonas aeruginosa, Haladaptatus paucihalophilus, Halomonas aquamarina*, or a combination thereof.

14. The biodegradable absorbent article as defined in claim 1, wherein the dehydrated polymer carrier comprises a crosslinked polyacrylate.

15. The biodegradable absorbent article as defined in claim 1, wherein the dehydrated polymer carrier comprises a starch-based polymer, a cellulose-based polymer, agarose, or a crosslinked polyvinyl alcohol polymer.

16. The biodegradable absorbent article as defined in claim 1, wherein the inactivated microorganism product is in the form of flakes.

17. The biodegradable absorbent article as defined in claim 1, wherein the inactivated microorganism product comprises particles, fibers, or a granular material.

18. The biodegradable absorbent article as defined in claim 1, wherein at least 90% of the microorganisms contained in the inactivated microorganism product are viable.

19. A kit of parts for disposing of a biodegradable absorbent article, comprising:

a biodegradable absorbent article according to claim 1;

a container; and a salt-containing liquid.

20. A method of degrading a biodegradable absorbent article, comprising:

contacting a biodegradable absorbent article according to claim 1 with a salt containing liquid.

21. The method of claim 20, wherein the biodegradable absorbent article is contacted with a bodily fluid, with a liquid having a salt content of from about of from about 100 millimolar to about 4 molar, or with both a bodily fluid and a liquid having a salt content of from about of from about 100 millimolar to about 4 molar.

22. The method of claim 21, wherein the biodegradable article is a wearable absorbent article, and contacted with the bodily fluid during use by a user.

23. The method of claim 20, wherein the biodegradable article is placed into a container that contains the liquid having a salt content of about 3 molar or greater.

* * * * *